United States Patent
Lin et al.

(10) Patent No.: US 7,429,492 B2
(45) Date of Patent: Sep. 30, 2008

(54) MULTIWELL PLATES WITH INTEGRATED BIOSENSORS AND MEMBRANES

(75) Inventors: Bo Lin, Lexington, MA (US); Gangadhar Jogikalmath, Cambridge, MA (US); Timothy Smith, Dracut, MA (US); Kurt Albertson, Littleton, MA (US); Christine Genick, Waltham, MA (US); Lance Laing, Belmont, MA (US)

(73) Assignee: SRU Biosystems, Inc., Woburn, MA (US)

( * ) Notice: Subject to any disclaimer, the term of this patent is extended or adjusted under 35 U.S.C. 154(b) by 0 days.

(21) Appl. No.: 11/566,818

(22) Filed: Dec. 5, 2006

(65) Prior Publication Data

US 2008/0020480 A1    Jan. 24, 2008

Related U.S. Application Data

(63) Continuation-in-part of application No. 10/667,696, filed on Sep. 22, 2003, now Pat. No. 7,264,973, which is a continuation-in-part of application No. 10/237,641, filed on Sep. 9, 2002, now Pat. No. 7,153,702.

(51) Int. Cl.
    *G01N 33/543* (2006.01)
(52) U.S. Cl. ............... 436/518; 422/57; 422/58; 422/82.11; 435/5; 435/6; 435/7.2; 435/7.32; 435/287.1; 435/287.2; 435/288.4; 435/288.7; 435/810; 436/164; 436/512; 436/524; 436/525; 436/805; 436/809; 436/815
(58) Field of Classification Search ............... None
    See application file for complete search history.

(56) References Cited

U.S. PATENT DOCUMENTS

| | | | |
|---|---|---|---|
| 3,689,346 A | 9/1972 | Rowland | 156/245 |
| 3,810,688 A | 5/1974 | Ballman et al. | 350/96 |
| 3,856,404 A | 12/1974 | Hershler et al. | 156/361 |
| 4,009,933 A | 3/1977 | Firester | |
| 4,050,895 A | 9/1977 | Hardy et al. | 436/527 |
| 4,240,751 A | 12/1980 | Linnecke et al. | 356/409 |
| 4,289,371 A | 9/1981 | Kramer | 350/3.71 |
| 4,344,438 A | 8/1982 | Schultz | 128/633 |
| 4,420,502 A | 12/1983 | Conley | 427/54.1 |
| 4,536,608 A | 8/1985 | Sheng et al. | |
| 4,560,248 A | 12/1985 | Cramp et al. | 385/12 |
| 4,576,850 A | 3/1986 | Martens | |
| 4,608,344 A | 8/1986 | Carter et al. | 436/34 |
| 4,650,329 A | 3/1987 | Barrett et al. | 356/481 |

(Continued)

FOREIGN PATENT DOCUMENTS

CA    2394966    8/2001

(Continued)

OTHER PUBLICATIONS

U.S. Appl. No. 10/667,696, filed Sep. 2003, Lin et al.*

(Continued)

*Primary Examiner*—Christopher L Chin
(74) *Attorney, Agent, or Firm*—McDonnell Boehnen Hulbert & Berghoff LLP

(57) ABSTRACT

The invention provides compositions and methods of detecting binding of molecules to a biosensor. Compositions of the invention comprise a multiwell plate with an integrated biosensor and a membrane.

11 Claims, 8 Drawing Sheets

U.S. PATENT DOCUMENTS

| | | | |
|---|---|---|---|
| 4,652,290 A | 3/1987 | Cho et al. ............... 65/31 |
| 4,668,558 A | 5/1987 | Barber |
| 4,701,008 A | 10/1987 | Richard et al. ............ 385/132 |
| 4,810,658 A | 3/1989 | Shanks et al. ............ 436/172 |
| 4,815,843 A | 3/1989 | Tiefenthaler et al. ........ 356/128 |
| 4,818,710 A | 4/1989 | Sutherland et al. .......... 436/527 |
| 4,857,273 A | 8/1989 | Stewart et al. ............. 436/82 |
| RE33,064 E | 9/1989 | Carter ........................ 436/34 |
| 4,876,208 A | 10/1989 | Gustafson et al. ........... 436/531 |
| 4,882,288 A | 11/1989 | North et al. ................ 436/525 |
| 4,888,260 A | 12/1989 | Cowan ......................... 403/1 |
| 4,931,384 A | 6/1990 | Layton et al. ................ 435/7 |
| 4,952,056 A | 8/1990 | Tiefenthaler ............... 356/73.1 |
| 4,958,895 A | 9/1990 | Wells et al. .............. 350/96.12 |
| 4,992,385 A | 2/1991 | Godfrey ..................... 436/525 |
| 4,999,234 A | 3/1991 | Cowan ....................... 428/156 |
| 5,071,248 A | 12/1991 | Tiefenthaler et al. ........ 356/128 |
| 5,118,608 A | 6/1992 | Layton et al. ............... 435/7.1 |
| 5,155,785 A | 10/1992 | Holland et al. ............... 385/89 |
| 5,156,785 A | 10/1992 | Zdrahala ..................... 264/108 |
| 5,170,448 A | 12/1992 | Ackley et al. ................ 385/31 |
| 5,175,030 A | 12/1992 | Lu et al. ..................... 428/30 |
| 5,210,404 A | 5/1993 | Cush et al. .................. 250/216 |
| 5,229,614 A | 7/1993 | Anderson et al. ...... 250/370.12 |
| 5,242,828 A | 9/1993 | Bergström et al. .......... 435/291 |
| 5,268,782 A | 12/1993 | Wenz et al. ................... 359/81 |
| 5,310,686 A | 5/1994 | Sawyers et al. |
| 5,337,183 A | 8/1994 | Rosenblatt ................... 359/248 |
| 5,413,884 A | 5/1995 | Koch et al. .................... 430/5 |
| 5,442,169 A | 8/1995 | Kunz ..................... 250/227.21 |
| 5,455,178 A | 10/1995 | Fattinger .................... 436/164 |
| 5,475,780 A | 12/1995 | Mizrahi ........................ 385/37 |
| 5,478,527 A | 12/1995 | Gustafson et al. ............. 422/82 |
| 5,478,756 A | 12/1995 | Gizeli et al. ................ 436/527 |
| 5,492,840 A | 2/1996 | Malmquist et al. |
| 5,496,701 A | 3/1996 | Pollard-Knight ............ 435/7.4 |
| 5,559,338 A | 9/1996 | Elliott et al. ............. 250/492.1 |
| 5,598,267 A | 1/1997 | Sambles et al. ............. 356/369 |
| 5,598,300 A | 1/1997 | Magnusson et al. ......... 359/566 |
| 5,606,170 A | 2/1997 | Saaski et al. ............. 250/458.1 |
| 5,615,052 A | 3/1997 | Doggett ...................... 359/811 |
| 5,629,214 A | 5/1997 | Crosby ....................... 436/518 |
| 5,631,171 A | 5/1997 | Sandstrom et al. ........... 436/518 |
| 5,690,894 A | 11/1997 | Pinkel et al. ............... 422/68.1 |
| 5,691,846 A | 11/1997 | Benson, Jr. et al. ......... 359/530 |
| 5,732,173 A | 3/1998 | Bylander et al. ............... 385/49 |
| 5,738,825 A | 4/1998 | Rudigier et al. ............... 422/82 |
| 5,768,461 A | 6/1998 | Svetkoff et al. .............. 385/116 |
| 5,771,328 A | 6/1998 | Wortman et al. ............. 385/146 |
| 5,792,411 A | 8/1998 | Morris et al. ................ 264/400 |
| 5,801,390 A | 9/1998 | Shiraishi ................... 250/559.3 |
| 5,804,453 A | 9/1998 | Chen |
| 5,814,516 A | 9/1998 | Vo-Dinh ................. 435/287.2 |
| 5,814,524 A | 9/1998 | Walt et al. ................... 436/514 |
| 5,821,343 A | 10/1998 | Keogh |
| 5,846,843 A | 12/1998 | Simon |
| 5,864,641 A | 1/1999 | Murphy et al. ................ 385/12 |
| 5,922,550 A | 7/1999 | Everhart et al. ............ 435/7.21 |
| 5,925,878 A | 7/1999 | Challener |
| 5,955,335 A | 9/1999 | Thust et al. |
| 5,955,378 A | 9/1999 | Challener |
| 5,955,729 A | 9/1999 | Nelson et al. |
| 5,986,762 A | 11/1999 | Challener |
| 5,991,480 A | 11/1999 | Kunz et al. |
| 5,994,150 A | 11/1999 | Challener et al. |
| 5,998,298 A | 12/1999 | Fleming et al. |
| 6,035,089 A | 3/2000 | Grann et al. |
| 6,042,998 A | 3/2000 | Brueck et al. |
| 6,052,213 A | 4/2000 | Burt et al. ................... 359/237 |
| 6,076,248 A | 6/2000 | Hoopman et al. |
| 6,088,505 A | 7/2000 | Hobbs |
| 6,100,991 A | 8/2000 | Challener |
| 6,128,431 A | 10/2000 | Siminovitch ................ 385/147 |
| 6,146,593 A | 11/2000 | Pinkel et al. ............... 422/68.1 |
| 6,174,677 B1 | 1/2001 | Vo-Dinh ..................... 356/301 |
| 6,185,019 B1 | 2/2001 | Hobbs et al. .................. 359/30 |
| 6,200,737 B1 | 3/2001 | Walt et al. ................... 430/320 |
| 6,215,928 B1 | 4/2001 | Friesem et al. ................ 385/37 |
| 6,218,194 B1 | 4/2001 | Lyndin et al. ............... 436/518 |
| 6,235,488 B1 | 5/2001 | Tom-Moy et al. |
| 6,303,179 B1 | 10/2001 | Koulik et al. |
| 6,316,153 B1 | 11/2001 | Goodman et al. ............... 430/8 |
| 6,320,991 B1 | 11/2001 | Challener et al. |
| RE37,473 E | 12/2001 | Challener |
| 6,338,968 B1 | 1/2002 | Hefti |
| 6,340,598 B1 | 1/2002 | Herron et al. |
| 6,346,376 B1 | 2/2002 | Sigrist et al. |
| 6,377,721 B1 | 4/2002 | Walt et al. .................... 385/12 |
| 6,404,554 B1 | 6/2002 | Lee et al. .................... 359/576 |
| 6,449,097 B1 | 9/2002 | Zhu et al. .................... 359/576 |
| 6,558,957 B1 | 5/2003 | Roinestad et al. ........ 422/82.05 |
| 6,570,657 B1 | 5/2003 | Hoppe et al. ................. 356/445 |
| 6,579,673 B2 | 6/2003 | McGrath et al. ................ 435/5 |
| 6,587,276 B2 | 7/2003 | Daniell ....................... 359/622 |
| 6,661,952 B2 | 12/2003 | Simpson et al. ............... 385/37 |
| 6,707,561 B1 | 3/2004 | Budach et al. ............. 356/521 |
| 6,748,138 B2 | 6/2004 | Wang et al. .................... 385/37 |
| 6,902,703 B2 | 6/2005 | Marquiss et al. |
| 6,951,715 B2 | 10/2005 | Cunningham |
| 7,023,544 B2 | 4/2006 | Cunningham |
| 7,070,987 B2 | 7/2006 | Cunningham |
| 7,094,595 B2 | 8/2006 | Cunningham |
| 7,153,702 B2 | 12/2006 | Lin |
| 2002/0018610 A1 | 2/2002 | Challener et al. |
| 2002/0123050 A1 | 9/2002 | Poponin ..................... 356/301 |
| 2002/0127565 A1 | 9/2002 | Cunningham et al. |
| 2002/0135752 A1 | 9/2002 | Sokolov et al. ............... 356/39 |
| 2002/0168295 A1 | 11/2002 | Cunningham et al. |
| 2002/0171045 A1 | 11/2002 | Perraut |
| 2003/0003599 A1 | 1/2003 | Wagner et al. |
| 2003/0017580 A1 | 1/2003 | Cunningham et al. |
| 2003/0017581 A1 | 1/2003 | Li et al. |
| 2003/0026891 A1 | 2/2003 | Qiu et al. |
| 2003/0027327 A1 | 2/2003 | Cunningham et al. |
| 2003/0027328 A1 | 2/2003 | Cunningham et al. |
| 2003/0032039 A1 | 2/2003 | Cunningham et al. |
| 2003/0059855 A1 | 3/2003 | Cunningham et al. |
| 2003/0068657 A1 | 4/2003 | Lin et al. |
| 2003/0077660 A1 | 4/2003 | Pien et al. |
| 2003/0092075 A1 | 5/2003 | Pepper et al. |
| 2003/0113766 A1 | 6/2003 | Pepper et al. |
| 2003/0148542 A1 | 8/2003 | Pawlak |
| 2003/0210396 A1 | 11/2003 | Hobbs et al. ................. 356/416 |
| 2004/0011965 A1 | 1/2004 | Hodgkinson ................ 356/317 |
| 2004/0132172 A1 | 7/2004 | Cunningham et al. |
| 2004/0132214 A1 | 7/2004 | Lin et al. |
| 2004/0151626 A1 | 8/2004 | Cunningham et al. |
| 2006/0193550 A1 | 8/2006 | Wawro |
| 2006/0281077 A1 | 12/2006 | Lin |
| 2007/0054339 A1 | 3/2007 | Lin |

FOREIGN PATENT DOCUMENTS

| | | |
|---|---|---|
| CA | 2395318 | 8/2001 |
| CH | 6 690 50 A5 | 2/1989 |
| CH | 6 705 21 A5 | 6/1989 |
| EP | 0 075 353 | 3/1983 |
| EP | 0 112 721 | 7/1984 |
| EP | 0 326 219 | 1/1989 |
| EP | 0 517 777 | 5/1996 |
| EP | 0 660 924 | 9/1999 |
| FR | 2 801 977 | 12/1999 |
| GB | 2 156 970 A | 10/1985 |
| GB | 2 227 089 | 7/1990 |

| | | |
|---|---|---|
| WO | WO 81/00912 | 2/1981 |
| WO | WO 84/02578 | 7/1984 |
| WO | WO 86/07149 | 12/1986 |
| WO | WO 90/08313 | 7/1990 |
| WO | WO 91/13339 | 9/1991 |
| WO | WO 92/04653 | 3/1992 |
| WO | WO 92/21768 | 12/1992 |
| WO | WO 93/14392 | 7/1993 |
| WO | WO 95/03538 | 2/1995 |
| WO | WO 98/57200 | 12/1998 |
| WO | WO 99/09392 | 2/1999 |
| WO | WO 99/09396 | 2/1999 |
| WO | WO 99/54714 | 10/1999 |
| WO | WO 99/66330 | 12/1999 |
| WO | WO 00/23793 | 4/2000 |
| WO | WO 00/29830 | 5/2000 |
| WO | WO 01/04697 | 1/2001 |
| WO | WO 02/061429 | 8/2002 |

OTHER PUBLICATIONS

U.S. Appl. No. 10/237,641, filed Sep. 2002, Lin et al.*
U.S. Appl. No. 60/244,312, filed Oct. 30, 2000, Cunningham et al.
U.S. Appl. No. 60/283,314, filed Apr. 12, 2001, Cunningham et al.
U.S. Appl. No. 60/303,028, filed Jul. 3, 2001, Cunningham et al.
Brecht, et al., "Optical probes and transducers", *Biosensors & Bioelectronics* vol. 10, pp. 923-936 (1995).*.
Challener, et al., "A multilayer grating-based evanescent wave sensing technique", *Sensors and Actuators B*, 71, pp. 42-46 (2000).*.
Cowan, "Aztec surface-relief volume diffractive structure", *J. Opt. Soc. Am.*, vol. 7, No. 8, pp. 1529-1544 (1990).*.
Cowan, "Holographic honeycomb microlens", *Optical Engineering*, vol. 24, No. 5, pp. 796-802 (1985).*.
Cowan, "The Recording and Large Scale Replication of Crossed Holographic Grating Arrays using Multiple Beam Interferometry", *SPIE* vol. 503, Application, Theory, and Fabrication of Periodic Structures, pp. 120-129 (1984).*.
Cowan, et al., "The Recording and Replication of Holographic Micropatterns for the Ordering of Photographic Emulsion Grains in Film Systems", *J. Imaging Sci.*, vol. 31, No. 3, pp. 100-107 (1987).*.
Cunningham, B. et al., "A plastic colorimetric resonant optical biosensor for multiparallel detection of label-free biochemical interactions", *Sensors and Actuators* B 85; pp. 219-226 (2002).*.
Cunningham, B. et al., "Colorimetric resonant reflection as a direct biochemical assay technique", *Sensors and Actuators* B 81; pp. 316-328 (2002).*.
Cunningham, "Optically Based Energy Transduction", *Techniques in Analytical Chemistry*, pp. 260-291.*.
Hobbs, et al., "Automated Interference Lithography Systems for Generation of Sub-Micron Feature Size Patterns", *SPIE*, vol. 3879, pp. 124-135, (1999).*.
Huber, et al., "Direct optical immunosensing *sensitivity and selectivity)", *Sensors and Actuators* B, 6, pp. 122-126 (1992).*.
Jenison, et al., "Interference-based detection of nucleic acid targets on optically coated silicon", *Nature Biotechnology*, vol. 19, pp. 62-64 (2001).*.
Jin, et al., "A biosensor concept based on imaging ellipsometry for visualization of biomolecular interactions", *Analytical Biochemistry*, vol. 232, pp. 69-72 (1995).*.
Jordan, et al., "Surface Plasmon Resonance Imaging Measurements of Electrostatic Biopolymer Adsorption onto Chemically Modified Gold Surfaces", *Analytical Chemistry*, vol. 69, No. 7, pp. 1449-1456 (1997).*.
Lin, et al., "A Porous Silicon-Based Optical Interferometric Biosensor", *Science*, vol. 278, pp. 840-843 (1997).*.
Magnusson, et al., "New principle for optical filters", *Appl. Phys. Lett.*, vol. 61, No. 9, pp. 1022-1024 (1992).
Magnusson, et al., "Transmission bandpass guided-mode resonance filters", *Applied Optics*, vol. 34, No. 35, pp. 8106-8109 (1995).*.
Morhard, et al., "Immobilization of antibodies in micropatterns for cell detection by optical diffraction", *Sensors and Actuators* B 70, pp. 232-242 (2000).*.

Pandey, et al., "Proteomics to study genes and genomes", *Nature* 405(6788):837-46 (2000).*.
Patel, et al., "Electrically tuned and polarization insensitive Fabry-Perot etalon with a liquid-crystal film", *Appl. Phys. Lett.*, vol. 58, No. 22, pp. 2491-2493 (1991).*.
Bertoni, et al., "Frequency-Selective Reflection and Transmission by a Periodic Dielectric Layer", *IEEE Transactions on Antennas and Propagation*, vol. 37, No. 1, pp. 78-83 (1989)*.
Brundrett, et al., "Normal-incidence guided-mode resonant grating filters: design and experimental demostration", *Optic Letters*, vol. 23, No. 9, pp. 700-702 (1998)*.
Peng, "*Polarization-control Components and Narrow-band Filters Based on Subwavelength Grating Structuures*" 1996*.
Statement of Applicants dated May 10, 2004*.
Leanu, Torben, *Material, Silicon Nitride*, 1996, 97, 98*.
Cerac, Technical publications: *Tantalum Oxide, $Ta_2O_5$ for Optical Coating*, 2000, Cerac, Inc.*.
Neuschafer et al., Evanescent resonator chips: a universal platform with superior sensitivity for fluorescence-based microarrays. Biosensors & Bioelectronics, 18 (2003) 489-497.*.
Budach et al., Generation of transducers for fluorescence-based microarrays with enhanced sensitivity and their application for gene expression profiling. Analytical Chemistry. Jun. 1, 2003;75(11):2571-7.*.
Anderson, et al., "Proteomics: applications in basic and applied biology", *Current Opinion in Biotechnology*, 2000, 11:408-412*.
MacBeath, et al., "Printing Proteins as Microarrays for High-Throughput Function Determination", *Science*, vol. 289, pp. 1760-1763, 2000*.
deWildt, et al., "Antibody arrays for high-throughput screening of antibody-antigen interactions", *Nature Biotechnology*, vol. 18, pp. 989-994, 2000*.
Cunningham et al., "A plastic colorimetric resonant optical biosensor for multiparallel detection of label-free biochemical interactions", *Sensors and Actuators B*, 85 (2002) 219-226*.
Caruso, et al., "Quartz Crystal Microbalance Study of DNA Immobilization and Hybridization for Nucleic Acid Sensor Development", *Analytical Chemistry*, vol. 69, No. 11, pp. 2043-2049, 1997*.
Hefti, et al, "Sensitive detection method of dielectric dispersions in aqueous-based, surface-bound macromolecular structures using microwave spectroscopy", *Applied Physics Letters*, vol. 75, No. 12, pp. 1802-1804, 1999*.
Wu, et al., "Bioassay of prostate-specific antigen (PSA) using microcantilevers", *Nature Biotechnology*, vol. 19, pp. 856-860, 2001*.
Wasserman, et al., "Structure and Reactivity of Alkylsiloxane Monolayers Formed by Reaction of Alkyltrichlorosilanes on Silicon Substrates", *Langmuir*, 5, 1074-1087, 1989*.
Kallury, et al., "X-ray Photoelectron Spectroscopy of Silica Surfaces Treated with Polyfunctional Silanes", *Anal. Chem.*, 60, 169-172, 1988*.
Cunningham, et al., "Colorimetric resonant reflection as a direct biochemical assay technique", *Sensors and Actuators B*, 81 (2002) 316-328*.
Mullaney, et al., "Epitope Mapping of Neutralizing Botulinum Neurotoxin A Antibodies by Phage Display", *Infection and Immunity*, vol. 69, No. 10, pp. 6511-6514, 2001*.
Nellen, et al., "Integrated Optical Input Grating Couplers as Biochemical Sensors", *Sensors and Actuators*, 15 (1988) 285-295*.
Lukosz and Tiefenthaler, "Embossing technique for fabricating integrated optical components in hard inorganic waveguiding materials," *Optics Letters*, vol. 8, pp. 537-539 (1983)*.
Tiefenthaler and Lukosz, "Integrated optical switches and gas sensors," *Optics Letters*, vol. 10, pp. 137-139 (1984)*.
Chabay, "Optical Waveguides," *Analytical Chemistry*, vol. 54, pp. 1071A-1080A (1982)*.
Sutherland et al., "Optical Detection of Antibody-Antigen Reactions at a Glass-Liquid Interface," *Clin. Chem.*, vol. 30, pp. 1533-1538 (1984)*.
Holm and Palik, "Internal-reflection spectroscopy," *Laser Focus*, vol. 15, pp. 60-65 (Aug. 1979)*.
Harrick and Loeb, "Multiple Internal Reflection Fluorescence Spectrometry," *Analytical Chemistry*, vol. 45, pp. 687-691 (1973)*.

Tien, "Light Waves in Thin Films and Integrated Optics," *Applied Optics*, vol. 10, pp. 2395-2413 (1971)*.

Dakss et al., "Grating Coupler for Efficient Excitation of Optical Guided Waves in Thin Films," *Applied Physics Letters*, vol. 16, pp. 523-525 (1970)*.

Sutherland et al., "Immunoassays at a Quartz-Liquid Interface: Theory, Instrumentation and Preliminary Application to the Fluorescent Immunoassay of Human Immunoglobulin G," *Journal of Immunological Methods*, vol. 74, pp. 253-265 (1984)*.

English translation of CH 670 521 A5*.

English of CH 669 050 A5*.

Patel, et al., "Multi-vwavelength Tunable Liquid-Crystal Etalon Filter", *IEEE Photonics Technology Letters*, vol. 3, No. 7, pp. 643-644 (1991).

Patterson, S.D., "*Proteomics: the industrialization of protein chemistry*", *Current Opinions in Biotechnology*. 11(4):413-8 (2000).*.

Peng, et al., "*Experimental demonstration of resonant anomalies in diffraction from two-dimensional gratings*", *Optics Letters* vol. 21, No. 8, pp. 549-551 (1996).*.

Peng, et al., "Resonant scattering from two-dimensional gratings", *J. Opt. Soc. Am. A.*, vol. 13, No. 5, pp. 993-1005 (1996).*.

Raguin, et al., "Structured Surfaces Mimic Coating Performance", *Laser Focus World*, pp. 113-117 (1997).*.

Sigal, et al., "A Self-Assembled Monolayer for the Binding and Study of Histidine-Tagged Proteins by Surface Plasmon Resonance", *Analytical Chemistry*, vol. 68, No. 3, pp. 490-497 (1996).*.

Wang, et al., "Design of waveguide-grating filters with symmetrical line shapes and low sidebands", *Optical Society of America*, vol. 19, No. 12, 919-921 (1994).*.

Wang, et al., "Guided-mode resonances in planar dielectric-layer diffraction gratings", *J. Opt. Soc. Am.*, vol. 7, No. 8, pp. 1470-1474 (1990).*.

Wang, et al., "Theory and applications of guided-mode resonance filter", *Applied Optics*, vol. 32, No. 14, pp. 2606-2613 (1993).*.

International Search Report for foreign counterpart application PCT/US01/50723, Sep. 17, 2002.*.

International Search Report for foreign counterpart application PCT/US03/01175, Aug. 18, 2003.*.

Invitation to Pay Additional Fees in foreign counterpart application PCT/US01/50723, Aug. 30, 2002.

Haider, "Zero-Order Gratings Used as an Artificial Distributed Index Medium", *Optik Wissenschaftliche Verlag GmbH*, Stuggart, DE, vol. 89, No. 3, pp. 107-112, 1992.

Peng, et al., "Experimental Demonstration of Resonant Anomalies in Diffraction from two-Dimensional Gratings", *Optics Letters, Optical Society of America*, vol. 21, No. 9, pp. 549-551, 1996.

Wilson, et al., "The Optical Properties 1-19 of 'Moth Eye' Antireflection Surfaces", *Optica ACTA*, vol. 29, No. 7, pp. 993-1009, 1982.

Bagnich, et al., "*Tunable Optical Filter*", Derwent Publications, English Translation, Abstract Only, Derwent Publications Ltd.

*Corning, Inc. v. SRU Biosystems, Inc.*, Memorandum Opinion dated Nov. 15, 2005 in the United States District Court for the district of Delaware*.

Liu, et al., "*Development of an optical fiber lactate sensor*", Mikrochimica Acta, 1999, 131(1-2), pp. 129-135*.

U.S. Appl. No. 11/635,934, filed Dec. 8, 2006.

European Search Report for EP 07 11 8355 dated Feb. 5, 2003.

Nelson, et al., "BIA/MS of Epitope-Tagged Peptides Directly from *E. Coli* Lysate: Multiplex Detection and Protein Identification at Low-Femtomole to Subfemtomole Levels" Anal. Chem. 1999, 71, 2858-2865.

Moffatt, "Optical Probes May Hasten Shift of Diagnostics from the Lab to Doc's Office" Genetic Engineering News, vol. 18 (1986) page 18.

Williams, et al., "The integration of SPR biosensors with mass spectrometry: possible applications for the proteome analysis", Trends in Microbiology, Elsevier, vol. 18, No. 2, (2000) pp. 45-48.

* cited by examiner

MULTIWELL PLATES WITH INTEGRATED BIOSENSORS AND MEMBRANES

This application is a continuation in part of U.S. Ser. No. 10/667,696, filed Sep. 22, 2003, now U.S. Pat. No. 7,264,973, which is a continuation in part of U.S. Ser. No. 10/237,641, filed Sep. 9, 2002, now U.S. Pat. No. 7,153,702.

BACKGROUND OF THE INVENTION

New drugs are tested to determine their toxicity, pharmacokinetics (PK) and adsorption, distribution, metabolism and excretion (ADME), profiles within animal or model systems. It is preferred that these studies are done in vitro prior to in vivo tests. Multiwell insert devices have an upper chamber, which is separated from a lower chamber by a membrane, and can be used to conduct such studies. See, e.g., US 2004/0091397. The upper chamber and membrane are part of a unit that can be removed from the apparatus forming the lower chamber.

ADME studies can include, e.g., cell migration assays, wherein cells are placed in the upper chamber of a multiwell insert device and allowed to migrate through the membrane into the lower chamber. The cells are detected via staining or fluorescent labels, which can be expensive and time consuming.

Additionally, drug adsorption assays can be performed with multiwell insert devices. Drug adsorption assays determine permeability of drugs across the membrane. Detection of the drug is often accomplished by liquid chromatography followed by mass spectrometry (LC/MS) and by UV visible spectrophotometry. However, these detection methods are cumbersome, have low throughput, can require large amounts of sample, and are end-point assays.

Therefore, methods are needed in the art that do not require labels, is high throughput, and can detect changes in real-time.

SUMMARY OF THE INVENTION

One embodiment of the invention provides a multiwell plate comprising a colorimetric resonant reflectance biosensor or a grating-based waveguide biosensor, a first liquid impermeable sheet of a thickness of about 5 µm to about 1,000 µm, wherein the first liquid impermeable sheet has two or more holes; wherein the first liquid impermeable sheet is attached to a top surface of the colorimetric resonant reflectance biosensor or the grating-based waveguide biosensor, a membrane attached to the top of the first liquid impermeable sheet, wherein the membrane covers all of the holes of the first liquid impermeable sheet, a multiwell plate frame attached to the top of the membrane, wherein the multiwell plate frame has two or more holes and wherein the holes have a same size, number, and position as in the first liquid impermeable sheet such that a multiwell plate with an upper chamber and a lower chamber is formed by the colorimetric resonant reflectance biosensor or the grating-based waveguide biosensor, the first liquid impermeable sheet, the membrane, and the multiwell plate frame.

The colorimetric resonant reflectance biosensor or the grating-based waveguide biosensor, the first liquid impermeable sheet, the membrane, and the multiwell plate frame can all be permanently attached to each other. Alternatively, the colorimetric resonant reflectance biosensor or the grating-based waveguide biosensor and the first liquid impermeable sheet can be separated from the membrane and the multiwell plate frame.

A second liquid impermeable sheet can occur between the multiwell plate frame and the membrane, wherein the second liquid impermeable sheet has holes with a same size, number, and position as in the first liquid impermeable sheet and the multiwell plate frame. The second liquid impermeable sheet can have a thickness of about 5 µm to about 1,000 µm.

The liquid impermeable sheets can be comprised of pressure sensitive adhesive, glass or plastic. The membrane can be comprised of nylon, polyester, or polycarbonate, polysulphone and other membrane forming materials known in the art. One or more specific binding substances or linkers can be immobilized on the surface of the biosensor.

Another embodiment of the invention provides a method of detecting molecules that pass through an upper chamber of the multiwell plate to the lower chamber. The method comprises:

(a) detecting a first peak wavelength value (PWV) or a first effective refractive index for the lower chamber of a well of the multiwell plate;

(b) placing a test sample in the upper chamber of a well of the multiwell plate of claim 1;

(c) incubating the test sample;

(d) detecting a second PWV or a second effective refractive index for the lower chamber of a well of the multiwell plate; and (e) comparing the first and second PWV or the first and second effective refractive index, wherein molecules that pass through an upper chamber of the multiwell plate are detected. The second PWV can be detected in real-time. Additional PWVs can also be detected. The molecules can be, e.g., a nucleic acid, peptide, protein solution, peptide solution, single or double stranded DNA, RNA, or RNA-DNA hybrid solution, a solution containing compounds from a combinatorial chemical library, a drug, antigen, polyclonal antibody, monoclonal antibody, single chain antibody (scFv), F(ab) fragment, F(ab')$_2$ fragment, Fv fragment, small organic molecule, large organic molecules, cell, virus, bacteria, polymer, nanoparticle, quantum dot, biological sample, or a combination thereof.

Therefore the invention provides methods of detecting molecules that pass through an integrated membrane of a multiwell plate that do not require labels, are high throughput, and can detect changes in real-time.

BRIEF DESCRIPTION OF THE DRAWINGS

FIG. 3A shows a view of the assembly of a device of the invention; FIG. 3B shows the assembled device from the bottom; FIG. 3C shows a top view of the a device of the invention; FIG. 3D shows a side, cut-away view of a device of the invention; FIG. 3E shows a side, cut-away view of 1 well of a device of the invention.

DETAILED DESCRIPTION OF THE INVENTION

Figure 1A:
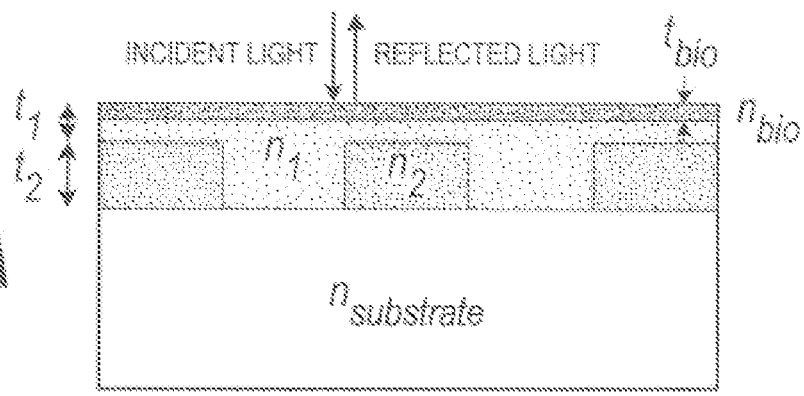
FIG. 1A shows a cross-sectional view of a biosensor wherein light is shown as illuminating the bottom of the biosensor; however, light can illuminate the biosensor from either the top or the bottom.

The instant invention provides a biosensor (101) that forms the bottom surface of a microwell plate (100). See FIG. 3A-E. A membrane (103) is integrated into the multiwell plate (100) such that each well (109) of the microwell plate (100) is divided into an upper chamber (107) and a lower chamber (108) by the membrane (103). The bottom surface of the upper chamber (107) is the membrane (103). The bottom surface of the lower chamber (108) is the biosensor (101). The biosensor (101) can be on a substrate (106) of, e.g., glass or plastic. The membrane (103) is an integral part of the multiwell plate (100) (such as 96, 384, or 1536 well microtiter plate). The membrane (103) allows for passage of moieties such as proteins, cells, drug molecules, or peptides from the upper chamber (107) to the lower chamber (108) where binding of the passed moieties elicits a response from the biosensor by binding to the surface of the biosensor through specific or non-specific binding. Particular examples of such measurements include screening of protein secretion (e.g., antibodies) or drug transport correlating to human adsorption (e.g., Caco-2 drug transport assay).

Since a membrane is integrated in to the multiwell plate no separate single well or multiwell inserts are necessary. See, e.g., US 2004/0091397. Manufacture of the microwell plates with integrated membranes is simple. The biosensor surface can be pre-functionalized with proteins or other activated molecules so that additional assay steps can be minimized.

Biosensors

Biosensors of the invention can be a colorimetric resonant biosensor and/or a grating-based waveguide biosensor. See e.g., Cunningham et al., "Colorimetric resonant reflection as a direct biochemical assay technique," Sensors and Actuators B, Volume 81, p. 316-328, Jan. 5 2002; U.S. Pat. Publ. No. 2004/0091397; U.S. Pat. No. 6,958,131; U.S. Pat. No. 6,787,110; U.S. Pat. No. 5,738,825; U.S. Pat. No. 6,756,078. Colorimetric resonant biosensors and grating-based waveguide biosensors are not surface plasmon resonant biosensors. SPR biosensors have a thin metal layer, such as silver, gold, copper, aluminum, sodium, and indium. The metal must have conduction band electrons capable of resonating with light at a suitable wavelength. The SPR biosensor surface exposed to light must be pure metal. Oxides, sulfides and other films interfere with SPR. Colorimetric resonant biosensors do not have a metal layer, rather they have a dielectric coating of high refractive index, such as $TiO_2$.

Colorimetric Resonant Reflectance Biosensors

A colorimetric resonant reflectance biosensor allows biochemical interactions to be measured on the biosensor's surface without the use of fluorescent tags, colorimetric labels or any other type of tag or label. A biosensor surface contains an optical structure that, when illuminated with collimated and/or white light, is designed to reflect only a narrow band of wavelengths. The narrow wavelength band is described as a wavelength "peak." The "peak wavelength value" (PWV) changes when materials, such as biological materials, are deposited or removed from the biosensor surface. A readout instrument is used to illuminate distinct locations on a biosensor surface with collimated and/or white light, and to collect collimated reflected light. The collected light is gathered into a wavelength spectrometer for determination of PWV.

A biosensor can be incorporated into standard disposable laboratory items such as microtiter plates by bonding the structure (biosensor side up) into the bottom of a bottomless microtiter plate cartridge. Incorporation of a biosensor into common laboratory format cartridges is desirable for compatibility with existing microtiter plate handling equipment such as mixers, incubators, and liquid dispensing equipment.

Colorimetric resonant reflectance biosensors comprise subwavelength structured surfaces are an unconventional type of diffractive optic that can mimic the effect of thin-film coatings. (Peng & Morris, "Resonant scattering from two-dimensional gratings," *J. Opt. Soc. Am. A*, Vol. 13, No. 5, p. 993, May 1996; Magnusson, & Wang, "New principle for optical filters," *Appl. Phys. Lett.*, 61, No. 9, p. 1022, August, 1992; Peng & Morris, "Experimental demonstration of resonant anomalies in diffraction from two-dimensional gratings," *Optics Letters*, Vol. 21, No. 8, p. 549, April, 1996). A SWS structure contains a one-dimensional, two-dimensional, or three dimensional grating in which the grating period is small compared to the wavelength of incident light so that no diffractive orders other than the reflected and transmitted zeroth orders are allowed to propagate. Propagation of guided modes in the lateral direction are not supported. Rather, the resonant grating effect occurs over a highly localized region of approximately 3 microns from the point that any photon enters the biosensor structure.

The reflected or transmitted light of a colorimetric resonant reflectance biosensor can be modulated by the addition of molecules such as specific binding substances or binding partners or both to the upper surface of the biosensor. The added molecules increase the optical path length of incident radiation through the structure, and thus modify the wavelength at which maximum reflectance or transmittance will occur.

In one embodiment, a colorimetric resonant reflectance biosensor, when illuminated with collimated and/or white light, is designed to reflect a single wavelength or a narrow band of wavelengths providing a "resonant grating effect". When specific binding substances are attached or added to the surface of the biosensor, the reflected wavelength is shifted due to the change of the optical path of light that is shown on the biosensor. By linking specific binding substances to a biosensor surface, complementary binding partner molecules can be detected without the use of any kind of fluorescent probe, particle label or any other type of label. The detection technique is capable of resolving changes of, for example, ~0.1 nm thickness of protein binding, and can be performed with the biosensor surface either immersed in fluid or dried.

A detection system consists of, for example, a light source that illuminates a small spot of a biosensor at normal incidence through, for example, a fiber optic probe, and a spectrometer that collects the reflected light through, for example, a second fiber optic probe also at normal incidence. Because no physical contact occurs between the excitation/detection system and the biosensor surface, no special coupling prisms are required and the biosensor can be easily adapted to any commonly used assay platform including, for example, microtiter plates. A single spectrometer reading can be performed (from the top or the bottom of the microtiter plate) in several milliseconds, thus it is possible to quickly measure a large number of molecular interactions taking place in parallel upon a biosensor surface, and to monitor reaction kinetics in real time.

Figure 1B:
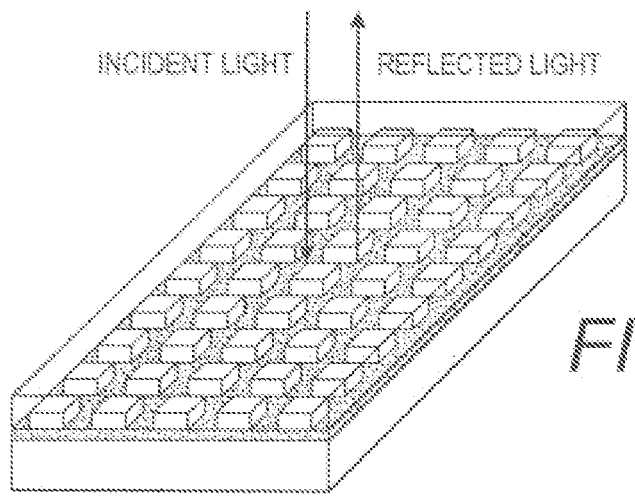
FIG. 1B shows a diagram of a biosensor wherein light is shown as illuminating the bottom of the biosensor; however, light can illuminate the biosensor from either the top or the bottom.

FIGS. 1A and 1B are diagrams of an example of a colorimetric resonant reflectance biosensor. In FIG. 1, $n_{substrate}$ represents a substrate material. $n_2$ represents the refractive index of an optical grating. $n_1$ represents an optional cover layer. $n_{bio}$ represents the refractive index of one or more specific binding substances. $t_1$ represents the thickness of the optional cover layer above the one-, two- or three-dimensional grating structure. $t_2$ represents the thickness of the grating. $t_{bio}$ represents the thickness of the layer of one or more specific binding substances. In one embodiment, are n2<n1 (see FIG. 1A). Layer thicknesses (i.e. cover layer, one or more specific binding substances, or an optical grating) are selected to achieve resonant wavelength sensitivity to additional molecules on the top surface. The grating period is selected to achieve resonance at a desired wavelength.

A colorimetric resonant reflectance biosensor comprises, e.g., an optical grating comprised of a high refractive index material, a substrate layer that supports the grating, and optionally, one or more specific binding substances or linkers immobilized on the surface of the grating opposite of the substrate layer. The high refractive index material has a higher refractive index than the substrate layer. Optionally, a cover layer covers the grating surface. An optical grating is coated with a high refractive index dielectric film which can be comprised of a material that includes, for example, zinc sulfide, titanium dioxide, tantalum oxide, and silicon nitride. A cross-sectional profile of a grating with optical features can comprise any periodically repeating function, for example, a "square-wave." An optical grating can also comprise a repeating pattern of shapes selected from the group consisting of lines (one-dimensional), squares, circles, ellipses, triangles, trapezoids, sinusoidal waves, ovals, rectangles, and hexagons. A colorimetric resonant reflectance biosensor of the invention can also comprise an optical grating comprised of, for example, plastic or epoxy, which is coated with a high refractive index material.

Figure 2:
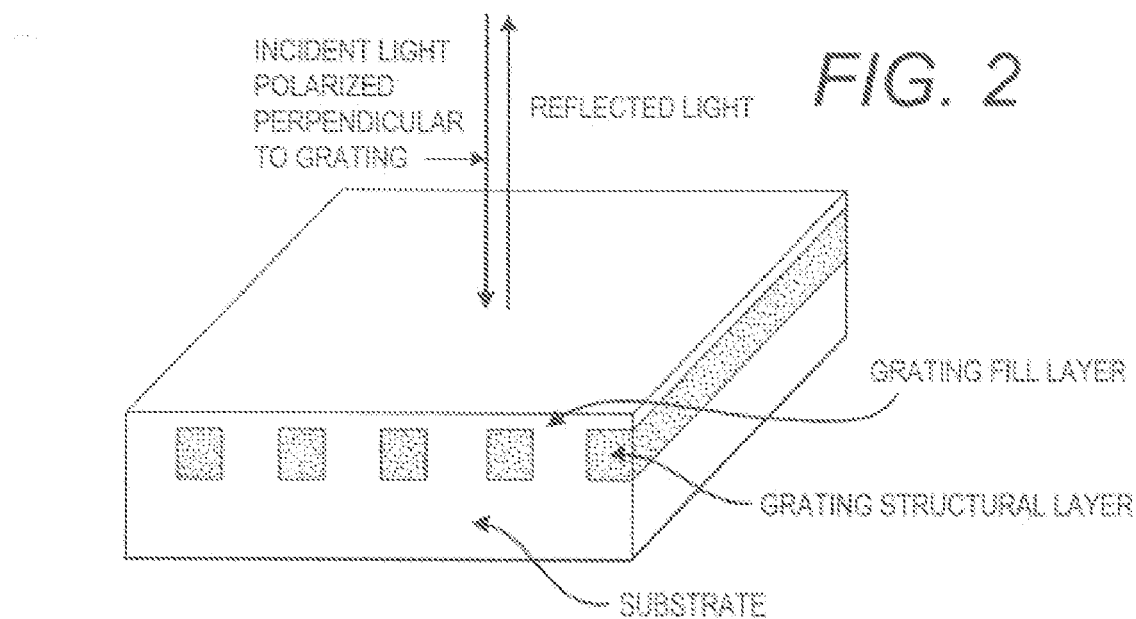
FIG. 2 shows an embodiment of a colorimetric resonant reflection biosensor comprising a one-dimensional grating.
Figure 3A:
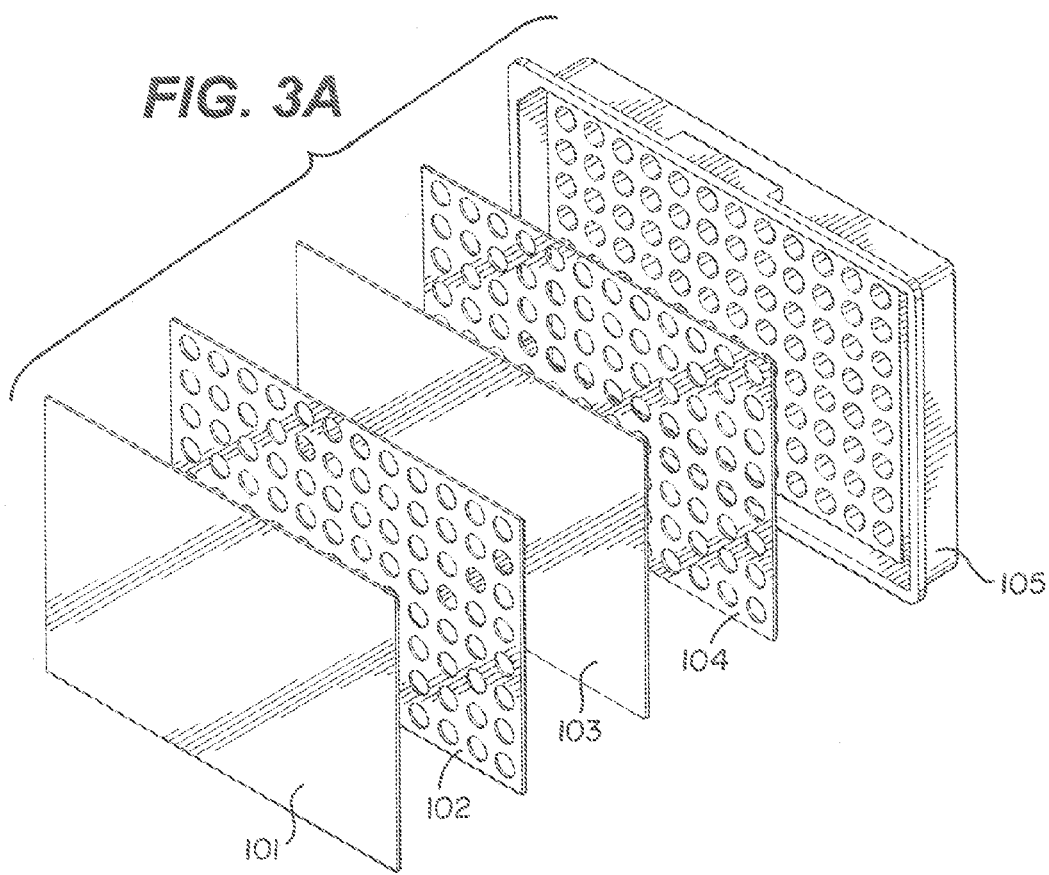
FIG. 3A-E.
Figure 3B:
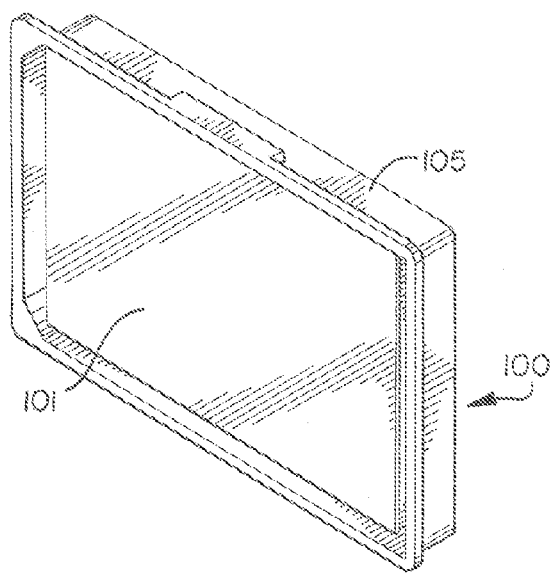
Figure 3C:
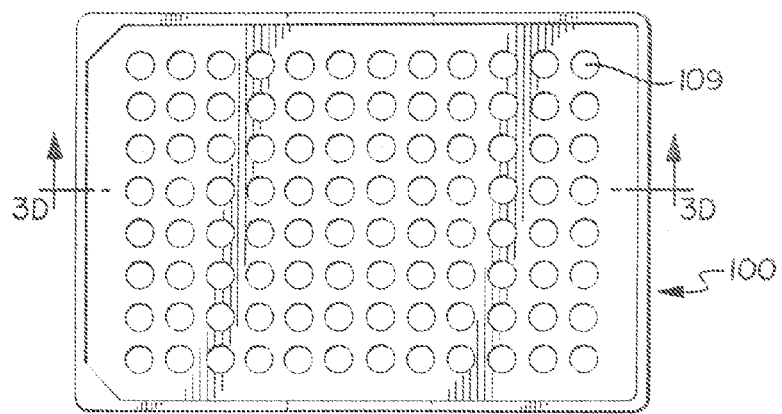
Figure 3D:
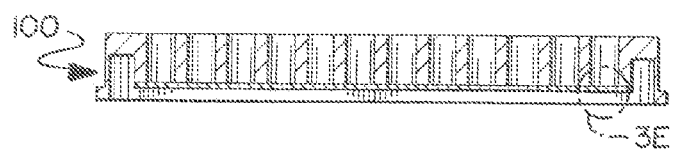
Figure 3E:
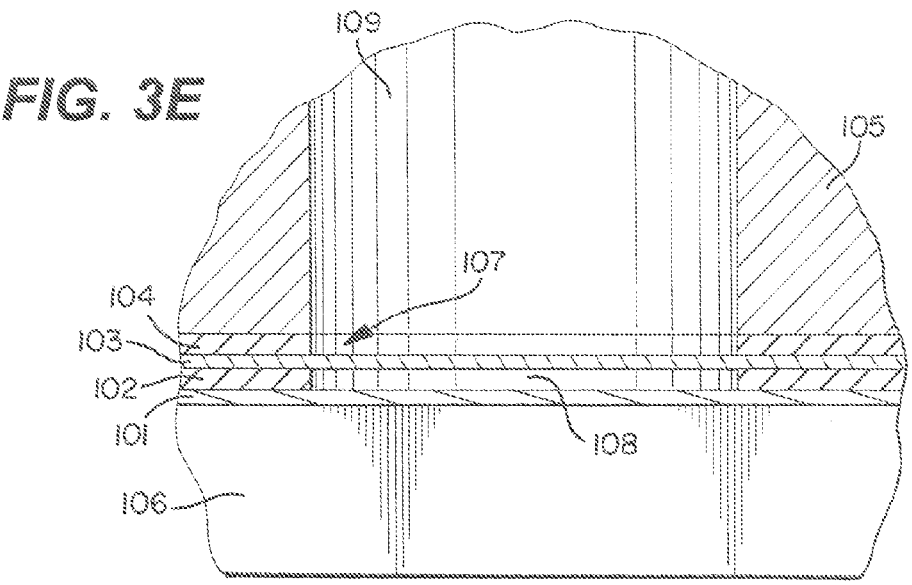

Linear gratings (i.e., one dimensional gratings) have resonant characteristics where the illuminating light polarization is oriented perpendicular to the grating period. A schematic diagram of one embodiment a linear grating structure with an optional cover layer is shown in FIG. 2. A colorimetric resonant reflection biosensor can also comprise, for example, a two-dimensional grating, e.g., a hexagonal array of holes or squares. Other shapes can be used as well. A linear grating has the same pitch (i.e. distance between regions of high and low refractive index), period, layer thicknesses, and material properties as a hexagonal array grating. However, light must be polarized perpendicular to the grating lines in order to be resonantly coupled into the optical structure. Therefore, a polarizing filter oriented with its polarization axis perpendicular to the linear grating must be inserted between the illumination source and the biosensor surface. Because only a small portion of the illuminating light source is correctly polarized, a longer integration time is required to collect an equivalent amount of resonantly reflected light compared to a hexagonal grating.

An optical grating can also comprise, for example, a "stepped" profile, in which high refractive index regions of a single, fixed height are embedded within a lower refractive index cover layer. The alternating regions of high and low refractive index provide an optical waveguide parallel to the top surface of the biosensor.

A colorimetric resonant reflectance biosensor of the invention can further comprise a cover layer on the surface of an optical grating opposite of a substrate layer. Where a cover layer is present, one or more specific binding substances can be immobilized on the surface of the cover layer opposite of the grating. Preferably, a cover layer comprises a material that has a lower refractive index than a material that comprises the grating. A cover layer can be comprised of, for example, glass (including spin-on glass (SOG)), epoxy, or plastic.

For example, various polymers that meet the refractive index requirement of a biosensor can be used for a cover layer. SOG can be used due to its favorable refractive index, ease of handling, and readiness of being activated with specific binding substances using the wealth of glass surface activation techniques. When the flatness of the biosensor surface is not an issue for a particular system setup, a grating structure of SiN/glass can directly be used as the sensing surface, the activation of which can be done using the same means as on a glass surface.

Resonant reflection can also be obtained without a planarizing cover layer over an optical grating. For example, a biosensor can contain only a substrate coated with a structured thin film layer of high refractive index material. Without the use of a planarizing cover layer, the surrounding medium (such as air or water) fills the grating. Therefore, specific binding substances are immobilized to the biosensor on all surfaces of an optical grating exposed to the specific binding substances, rather than only on an upper surface.

In general, a colorimetric resonant reflectance biosensor of the invention will be illuminated with white light that will contain light of every polarization angle. The orientation of the polarization angle with respect to repeating features in a biosensor grating will determine the resonance wavelength. For example, a "linear grating" (i.e., a one-dimensional grating) biosensor consisting of a set of repeating lines and spaces will have two optical polarizations that can generate separate resonant reflections. Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A biosensor can generally be designed to optimize the properties of only one polarization (the s-polarization), and the non-optimized polarization is easily removed by a polarizing filter.

In order to remove the polarization dependence, so that every polarization angle generates the same resonant reflection spectra, an alternate biosensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single sensor location—such as an array spot or a microtiter plate well. Each separate microarray spot or microtiter plate well has a separate concentric ring pattern centered within it. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron. The grating depth is about 0.01 to about 1 micron.

In another embodiment, an array of holes or posts are arranged to closely approximate the concentric circle structure described above without requiring the illumination beam to be centered upon any particular location of the grid. Such an array pattern is automatically generated by the optical interference of three laser beams incident on a surface from three directions at equal angles. In this pattern, the holes (or posts) are centered upon the corners of an array of closely packed hexagons. The holes or posts also occur in the center of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron.

A detection system can comprise a colorimetric resonant reflectance biosensor a light source that directs light to the colorimetric resonant reflectance biosensor, and a detector that detects light reflected from the biosensor. In one embodiment, it is possible to simplify the readout instrumentation by the application of a filter so that only positive results over a determined threshold trigger a detection.

By measuring the shift in resonant wavelength at each distinct location of a colorimetric resonant reflectance biosensor of the invention, it is possible to determine which distinct locations have material deposited on them. The extent of the shift can be used to determine, e.g., the amount of specific binding substances or binding partners in a test sample and the chemical affinity between one or more specific binding substances and binding partners of a test sample.

A colorimetric resonant reflectance biosensor can be illuminated twice. The first measurement determines the reflectance spectra of one or more distinct locations of a biosensor array with, e.g., nothing on the surface of the biosensor or with one or more specific binding substances or linkers immobilized on the biosensor. The second measurement determines the reflectance spectra after, e.g., one or more specific binding substances or binding partners are applied to a biosensor. The difference in peak wavelength between these two measurements is a measurement of the amount of specific binding substances or binding partners that are located on a biosensor or one or more distinct locations of a biosensor. This method of illumination can control for small imperfections in a surface of a biosensor that can result in regions with slight variations in the peak resonant wavelength. This method can also control for varying concentrations or molecular weights of specific binding substances immobilized on a biosensor.

Grating-Based Waveguide Biosensor

Grating-based waveguide biosensors are described in, e.g., U.S. Pat. No. 5,738,825. A grating-based waveguide biosensor comprises a waveguiding film and a diffraction grating that incouples an incident light field into the waveguiding film to generate a diffracted light field. A change in the effective refractive index of the waveguiding film is detected.

A grating-based waveguide biosensor can be formed of a substrate that is covered by a waveguiding film that has a higher refractive index than the substrate. The diffraction grating can be formed in the substrate, between the substrate and the waveguiding film, or in the waveguiding film. The diffraction grating can also be formed in the interface between the waveguiding film and the substrate.

The waveguiding film can be made of metal-oxide based materials such as $Ta_2O_5$, $TiO_2$, $TiO_2SiO_2$, $HfO_2$, $ZrO_2$, $Al_2O_3$, $Si_3N_4$, HfON, SiON, $Al_2O_3$ medium oxide, a mixture of $SiO_2$ and $TiO_2$ or one of the oxynitrides HfON or SiON, scandium oxide or mixtures thereof. Silicon nitrides or oxynitrides (for example $HfO_xN_y$) can also be used. A waveguiding film can have a refractive index in the range of about 1.6 to about 2.5. The thickness of the waveguiding film can be about 20 to about 1000 nm. The grating coupler can have a line density of about 1000 to about 3000 lines per mm. The substrate can be, e.g., glass or plastic (polycarbonate) and can have a refractive index of about 1.3 to about 1.7.

The waveguiding film can be coated with one or more specific binding substances or linkers. The specific binding substances can bind with one or more binding partners by covalent or non-covalent binding. The waveguiding film can also be coated with linkers or can have no coating.

A detection unit can comprise (i) at least one light source to generate and direct at least one incident light field onto the diffraction grating to provide mode excitation in the waveguiding film; (ii) at least one focusing means to focus the light field diffracted out of the waveguiding film; and (iii) at least one position sensitive detector to monitor the position of the focused light field.

The incident light field can be generated by a laser. More than one incident light field can be provided in a detection unit. For example, a light field can be provided for each column of the matrix of the detection cell. If more than one light field is provided, they may be generated by providing (i) more than one light source, (ii) by splitting the field of a single light source, or (iii) by expanding a light field. Similarly more than one light detector may be provided; one light detector for each light field.

Surface of Biosensor

One or more specific binding substances or linkers can be immobilized on a biosensor by for example, physical adsorption or by chemical binding. A specific binding substance can be, for example, a nucleic acid, peptide, protein solutions, peptide solutions, single or double stranded DNA solutions, single and double stranded RNA and or DNA solutions (such as one might find in polymerase complexes, gyrase or helicase complexes or RNAi complexes, RNA solutions, RNA-DNA hybrid solutions), solutions containing compounds from a combinatorial chemical library, a drug, antigen, polyclonal antibody, monoclonal antibody, single chain antibody (scFv), F(ab) fragment, F(ab')$_2$ fragment, Fv fragment, small organic molecule, cell, virus, bacteria, polymer, nanoparticle, quantum dot, or biological sample. A biological sample can be for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatic fluid. The polymer is selected from the group of long chain molecules with multiple active sites per molecule consisting of hydrogel, dextran, poly-amino acids and derivatives thereof, including poly-lysine (comprising poly-l-lysine and poly-d-lysine), poly-phe-lysine and poly-glu-lysine. A nanoparticle is a particle with at least one dimension that is less than about 200 nm. A quantum dot is a semiconductor crystal comprised of about 100 to about 1,000 electrons, which is about 2 to about 10 nanometers, or about 10 to about 50 atoms, in diameter. Nanoparticles and quantum dots can be conjugated to, e.g., one or more molecules, such as a linker, biological molecule, drug, or organic molecule.

A specific binding substance specifically binds to a binding partner that is added to the surface of a biosensor of the invention. A specific binding substance specifically binds to its binding partner, but does not substantially bind other binding partners added to the surface of a biosensor. For example, where the specific binding substance is an antibody and its binding partner is a particular antigen, the antibody specifically binds to the particular antigen, but does not substantially bind other antigens. A binding partner can be, for example, a nucleic acid, peptide, protein solutions, peptide solutions, single or double stranded DNA solutions, RNA solutions, single and double stranded RNA and or DNA solutions (such as one might find in polymerase complexes, gyrase or helicase complexes or RNAi complexes, RNA-DNA hybrid solutions), solutions containing compounds from a combinatorial chemical library, a drug, antigen, polyclonal antibody, monoclonal antibody, single chain antibody (scFv), F(ab) fragment, F(ab')$_2$ fragment, Fv fragment, small organic molecule, large organic molecules, cell, virus, bacteria, polymer, nanoparticle, quantum dot, or biological sample. A biological sample can be, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, and prostatic fluid.

Furthermore, one or more specific binding substances can be arranged in an array of one or more distinct locations on the biosensor surface, said surface residing within one or more wells of a multiwell plate and comprising one or more surfaces of the multiwell plate. The array of specific binding substances comprises one or more specific binding substances on the sensor surface within a microtiter plate well such that a surface contains one or more distinct locations, each with a different specific binding substance or with a different amount of a specific binding substance. For example, an array can comprise 1, 10, 100, 1,000, 10,000 or 100,000 distinct locations. Thus, each well of a multiwell plate can have within it an array of one or more distinct locations separate from the other wells of the multiwell plate, which allows multiple different samples to be processed on one multiwell plate of the invention. The array or arrays within any one well can be the same or different than the array or arrays found in any other microtiter wells of the same microtiter plate.

Immobilization of a specific binding substance can be affected via binding to, for example, the following functional linkers: a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. Furthermore, a specific binding substance can be immobilized on the surface of a biosensor via physical adsorption, chemical binding, electrochemical binding, electrostatic binding, hydrophobic binding or hydrophilic binding.

In one embodiment of the invention a biosensor can be coated with a linker such as, e.g., a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. For example, an amine surface can be used to attach several types of linker molecules while an aldehyde surface can be used to bind proteins directly, without an additional linker. A nickel surface can be used to bind molecules that have an incorporated histidine ("his") tag. Detection of "his-tagged" molecules with a nickel-activated surface is well known in the art (Whitesides, *Anal Chem.* 68, 490, (1996)).

Linkers and specific binding substances can be immobilized on the surface of a biosensor such that each well has the same linkers and/or specific binding substances immobilized therein. Alternatively, each well can contain a different combination of linkers and/or specific binding substances.

A binding partner or analyte can bind to a linker or specific binding substance immobilized on the surface of a biosensor. Alternatively, the surface of the biosensor can have no linker or specific binding substance and a binding partner or analyte can bind to the biosensor surface non-specifically.

Immobilization of one or more specific binding substances or linker onto a biosensor is performed so that a specific binding substance or linker will not be washed away by rinsing procedures, and so that its binding to binding partners in a test sample is unimpeded by the biosensor surface. Several different types of surface chemistry strategies have been implemented for covalent attachment of specific binding substances to, for example, glass for use in various types of microarrays and biosensors. These same methods can be readily adapted to a biosensor of the invention. Surface preparation of a biosensor so that it contains the correct functional groups for binding one or more specific binding substances is an integral part of the biosensor manufacturing process.

One or more specific binding substances can be attached to a biosensor surface by physical adsorption (i.e., without the use of chemical linkers) or by chemical binding (i.e., with the use of chemical linkers) as well as electrochemical binding, electrostatic binding, hydrophobic binding and hydrophilic binding. Chemical binding can generate stronger attachment of specific binding substances on a biosensor surface and provide defined orientation and conformation of the surface-bound molecules.

Immobilization of specific binding substances to plastic, epoxy, or high refractive index material can be performed essentially as described for immobilization to glass. However, the acid wash step can be eliminated where such a treatment would damage the material to which the specific binding substances are immobilized.

Multiwell Plate

The most common assay formats for pharmaceutical high-throughput screening laboratories, molecular biology research laboratories, and diagnostic assay laboratories are microtiter plates. The plates are standard-sized plastic cartridges that can contain about 2, 6, 8, 24, 48, 96, 384, 1536 or 3456 individual reaction vessels arranged in a grid. Due to the standard mechanical configuration of these plates, liquid dispensing, robotic plate handling, and detection systems are designed to work with this common format. A biosensor of the invention can be incorporated into the bottom surface of a standard microtiter plate. Because the biosensor surface can be fabricated in large areas, and because the readout system does not make physical contact with the biosensor surface, an arbitrary number of individual biosensor areas can be defined that are only limited by the focus resolution of the illumination optics and the x-y stage that scans the illumination/detection probe across the biosensor surface.

A multiwell plate of the invention can comprise a colorimetric resonant reflectance biosensor or a grating-based waveguide biosensor (101); a first liquid impermeable sheet (102) of a thickness of about 5 μm to about 1,000 μm, wherein the first liquid impermeable sheet (102) has two or more holes; wherein the first liquid impermeable sheet (102) is attached to a top surface of the colorimetric resonant reflectance biosensor or the grating-based waveguide biosensor (101), a membrane (103) attached to the top of the first liquid impermeable sheet (102), wherein the membrane (103) covers all of the holes of the first liquid impermeable sheet (102), and a second liquid impermeable sheet (104) of a thickness of about 5 μm to about 1,000 μm attached to the top of the membrane (103), wherein the second liquid impermeable sheet (104) has two or more holes and wherein the holes have a same size, number, and position as in the first liquid impermeable sheet (102) such that a multiwell plate with an upper chamber (107) (the space above the membrane) and a lower chamber (108) (the space below the membrane) is formed by the colorimetric resonant reflectance biosensor or the grating-based waveguide biosensor (101), the first liquid impermeable sheet (102), the membrane (103), and the second liquid impermeable sheet (104).

A multiwell plate frame (105) can be present on top of the second liquid impermeable sheet (104). However, the second liquid impermeable sheet (104) is not a necessary component of a device of the invention. The second liquid impermeable sheet (104) can serve to attach the multiwell plate frame (105) to the membrane (103) and to eliminate leaking of the wells. In the place of a second liquid impermeable sheet, liquid epoxy bonding, thermal bonding or the like could be used to attach the multiwell plate frame (105) to the membrane (103). Optionally, the second liquid impermeable sheet can be present with one or more other liquid impermeable sheets for attachment of the multiwell plate frame (105) to the membrane (103) or for other purposes. The multiwell plate frame (105) can add depth to the wells such that the upper chamber (107) can hold greater volumes of liquid than the upper chamber (107) which is formed only by the second liquid impermeable sheet (104). Alternatively, the multiwell plate frame can merely add mass to the apparatus so that it is easier to handle. The multiwell plate frame (105) can be made of plastic, glass, pressure sensitive adhesive or any other suitable material. The multiwell plate frame (105) has two or more holes, wherein the holes have a same size, number and position as in the first and second liquid impermeable sheets (102; 104). The biosensor (101), first liquid impermeable sheet (102), the membrane (103), and the second liquid impermeable sheet (104) can all be permanently attached to each other. The multiwell plate frame (105) can be permanently or non-permanently attached to the second liquid impermeable sheet (104). Alternatively, the second liquid impermeable sheet (104) and the membrane (103) can be removable from the biosensor (101) and first liquid impermeable sheet (102).

Several methods for attaching a biosensor of the invention to the bottom surface of bottomless microtiter plates can be used, including, for example, adhesive attachment, ultrasonic welding, and laser welding.

A liquid impermeable sheet can be, e.g., pressure sensitive adhesive, plastic, glass, or any other suitable material.

A membrane can be, e.g., nylon, polyester, polycarbonate, polysulphone or any other membrane forming materials known in the art. The pore size of the membrane can vary depending upon the use of the multiwell plate. In one embodiment, the pore size of the membrane is, e.g., about 0.1, 1, 2, 3, 4, 5, 6 7 8, 9, 10, 11, 12, 13 µm, or more. A membrane is part of the multiwell plate and can be assembled in the multiwell plate during the manufacturing of the multiwell plate.

Methods of Using Biosensors

Biosensors of the invention can be used to study one or a number of specific binding substance/binding partner interactions in parallel. Binding of one or more specific binding substances to their respective binding partners or analytes can be detected, without the use of labels, by applying one or more binding partners or analytes to a biosensor that have one or more specific binding substances immobilized on their surfaces. Alternatively, binding of specific binding substances that pass through the membrane of the multiwell plates can bind non-specifically to the biosensor via linkers or other non-specific binding. A colorimetric resonant reflectance biosensor is illuminated with light and a maxima in reflected wavelength, or a minima in transmitted wavelength of light is detected from the biosensor. For a grating-based waveguide biosensor a change in effective refractive index of the waveguide is detected. If one or more specific binding substances have bound to the biosensor via their respective binding partners, linkers, or other non-specific binding, or is merely deposited on a location of the biosensor, then the reflected wavelength of light is shifted or the effective refractive index is changed, as compared to a situation where one or more specific binding substances have not bound to their respective binding partners or linkers or have not been deposited on a location of the biosensor. Where a biosensor is coated with an array of one or more distinct locations containing the one or more specific binding substances, then a maxima in reflected wavelength or minima in transmitted wavelength of light or a change in effective refractive index is detected from each distinct location of the biosensor.

Molecules released from cells grown on a membrane of the invention can be detected. The membrane can be permeable to molecules secreted from cells cultured on its surface and can be impermeable to whole cells. This method can comprise the following steps: immobilizing one or more specific binding substances or linkers onto a surface of the biosensor at one or more distinct locations or in a well (or using a biosensor surface with no specific binding substances or linkers); detecting a PWV or effective refractive index of the one or more distinct locations or well; growing cells on the membrane; detecting the PWV or effective refractive index of the one or more distinct locations or well; and comparing the initial PWV or effective refractive index reading with the subsequent PWV or effective refractive index reading. Molecules that have moved to the surface of the biosensor are detected. Furthermore, the initial PWV or effective refractive index reading is a relative measure of the specific binding substance that is present on the biosensor, and the difference between the initial PWV or effective refractive index reading in relation to the subsequent PWV or effective refractive index reading is a relative measure of the molecules released from cells grown on the membrane that are bound to the specific binding substances or are merely present on the surface of the biosensor.

Advantageously, the detection can occur in real-time, i.e., as the assay is being run. Multiple time points or constant monitoring of PWVs of one or more locations of a biosensor can be monitored as specific binding substances move toward the biosensor and become located on the biosensor.

The method described above, that of detecting molecules released from cells grown on a membrane of the invention can also comprise alternative steps. For example, one or more binding substances can be immobilized in one or more distinct locations defining an array within a well of a microtiter plate, wherein the biosensor comprises an internal surface of the well. Detecting a PWV or effective refractive index reading for the one or more distinct locations defining an array within the well is followed by growing cells on a membrane of the invention. The final steps are detecting the PWV or effective refractive index for the one or more distinct locations within the well and comparing the initial PWV or effective refractive index reading with the subsequent PWV or effective refractive index reading. The difference between the initial PWV or effective refractive index reading in relation to the subsequent PWV or effective refractive index reading indicates the relative binding of one or more molecules secreted from the cells growing on the membrane within a well to the one or more specific binding substances immobilized at one or more distinct locations within the well on the surface of a biosensor.

The ability to detect the binding of binding partners or analytes to specific binding substances or linkers, optionally followed by the ability to detect the removal of substantially entire or partial bound specific binding substances, from one or more distinct locations or wells of the biosensor is an important aspect of the invention. Biosensors of the invention are also capable of detecting and quantifying the amount of a binding partner from a sample that is bound to one or more distinct locations defining an array by measuring the shift in reflected wavelength of light or effective refractive index. For example, the wavelength shift or effective refractive index reading at one or more distinct locations can be compared to positive and negative controls at other distinct locations to determine the amount of a specific binding substance that is bound. Importantly, numerous such one or more distinct locations can be arranged on the biosensor multiwell plate having about 2, 6, 8, 24, 48, 96, 384, 1536 or 3456 wells.

In one embodiment of the invention, the integrated membrane can separate, e.g., cells producing, e.g., antibodies, which are located in the upper chamber, from the biosensor surface in the lower chamber. The cells are grown on the top surface of the membrane in the upper chamber and molecules, such as antibodies, produced by the cells can pass through the membrane to the lower chamber. The membrane pore sizes can be adjusted from nanometers to tens of microns. Proteins or other molecules that pass through the membrane can specifically or non-specifically bind to the biosensor surface in the lower chamber. Therefore, non-specific signal due to cell binding to the biosensor surface can be eliminated and only signal from molecules traveling through the membrane and binding specifically or non-specifically to the biosensor can be detected.

In another embodiment of the invention components of a mixture can be separated using the membrane. Complex mixtures containing many sized components can be selectively passed through the membrane such that only components of a certain size pass to the lower chamber and specifically bind to or non-specifically bind to or are merely located on the biosensor surface. In one example of the quantitative employment of this embodiment, the device can be used to monitor the extent of an equilibrium dialysis method.

In another embodiment of the invention, the microwell plates of the invention can be used in cell migration assays. By carefully selecting the size of the pores in the membrane, a cell migration assay, such as a chemotaxis assay, can be performed by setting up a chemotractant gradient between the upper and lower chambers of the microwell plate. The cells can migrate to the chemotractant gradient in the lower chamber and the biosensor surface, where they can specifically or non-specifically bind to the biosensor surface. Detection systems comprised of an imaging spectrometer, or alternatively a fiber optic probe that can be moved to read from multiple locations of the biosensor, can then be used to detect the location of the cells, and in turn permit the computation of the cell migration velocity.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims. In addition, where features or aspects of the invention are described in terms of Markush groups or other grouping of alternatives, those skilled in the art will recognize that the invention is also thereby described in terms of any individual member or subgroup of members of the Markush group or other group.

EXAMPLE

Figure 4:
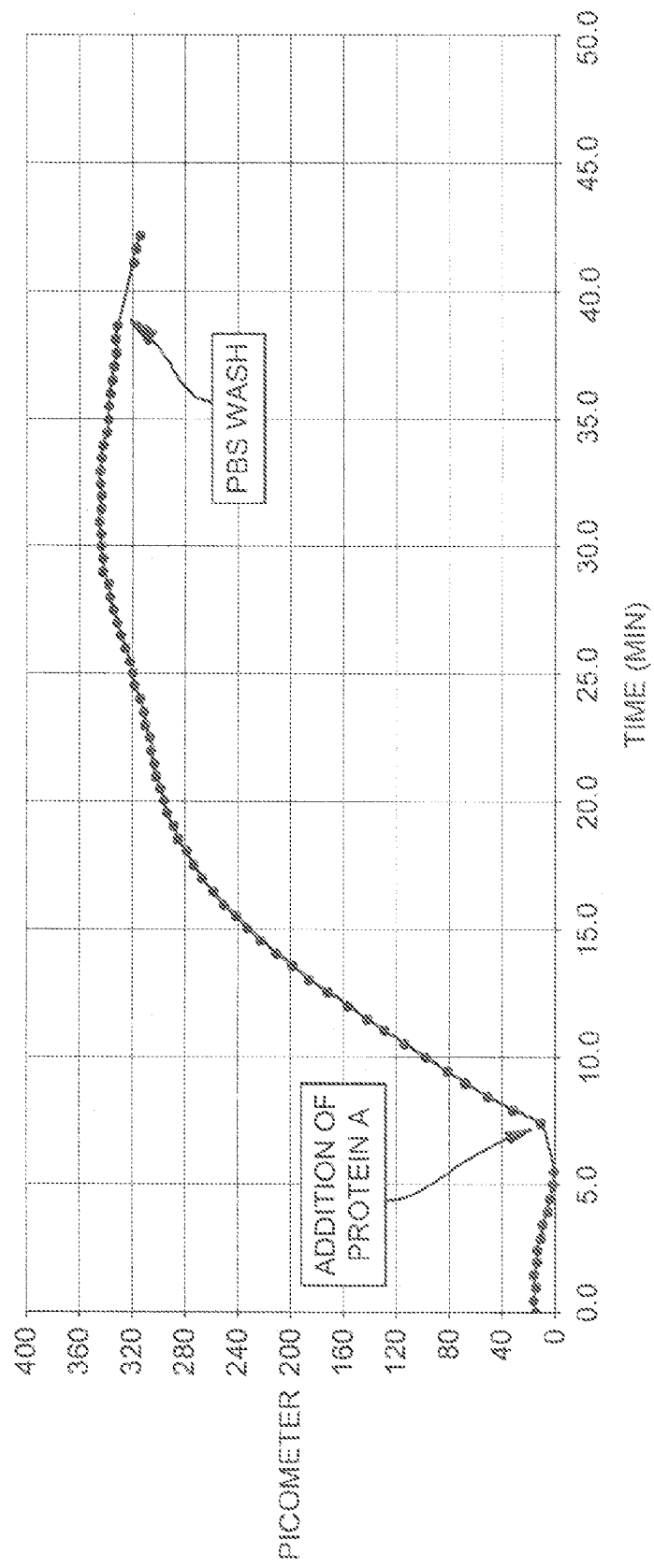
FIG. 4 shows the results of an assay performed with Protein A.
Figure 5:
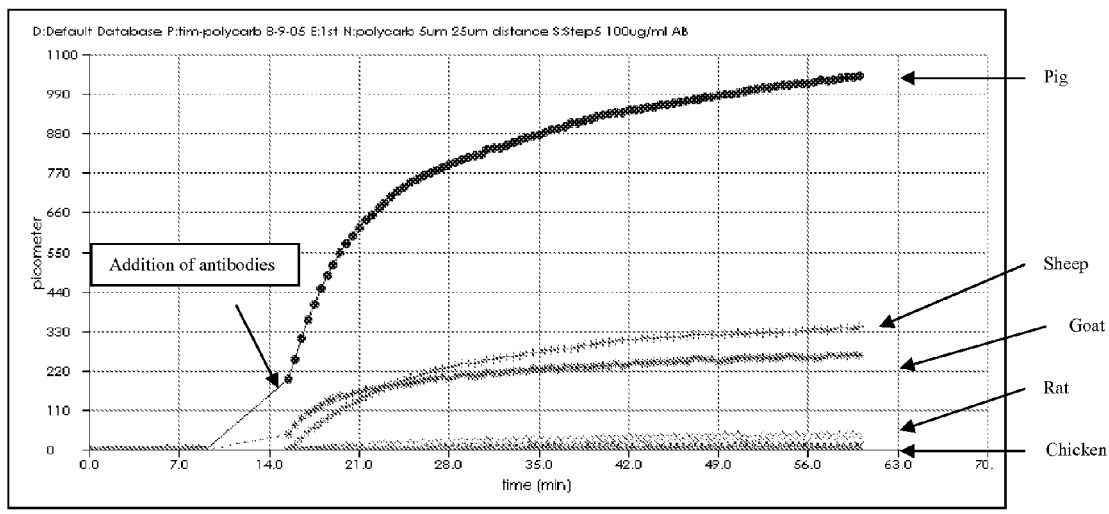
FIG. 5 shows the results of an assay performed with several antibodies.
Figure 6:
FIG. 6 shows an endpoint assay performed with pig, goat, sheep and rat IgG.

A multiwell plate of the invention was constructed with a 5 μm integrated membrane and a 25 μm distance between a colorimetric resonant reflectance biosensor surface and the membrane. A baseline PWV was taken with PBS. The PBS was removed and 50 μL of a 20 μg/mL Protein A solution was added. The Protein A diffused through the membrane and bound to the biosensor surface causing a response in signal. See FIG. 4. A PBS wash was used to remove any unbound Protein A from the well. A baseline PWV was taken with PBS in another multiwell plate of the invention. A. The PBS was removed and 50 μL of pig, sheep, goat, rat and chicken antibodies at 100 μg/mL was added. The antibodies diffused through the membrane and bound to Protein A, which was on the biosensor surface. The affinity of the antibodies to Protein A is pig>sheep>goat>rat>chicken, as demonstrated by FIG. 5. 100 μg/mL of pig, goat, sheep and rat IgG was added to the biosensor and an endpoint assay was done. See FIG. 6. The first column is pig, the second is goat, the third is sheep, the fourth is rat, and the fifth is PBS.

Figure 7:
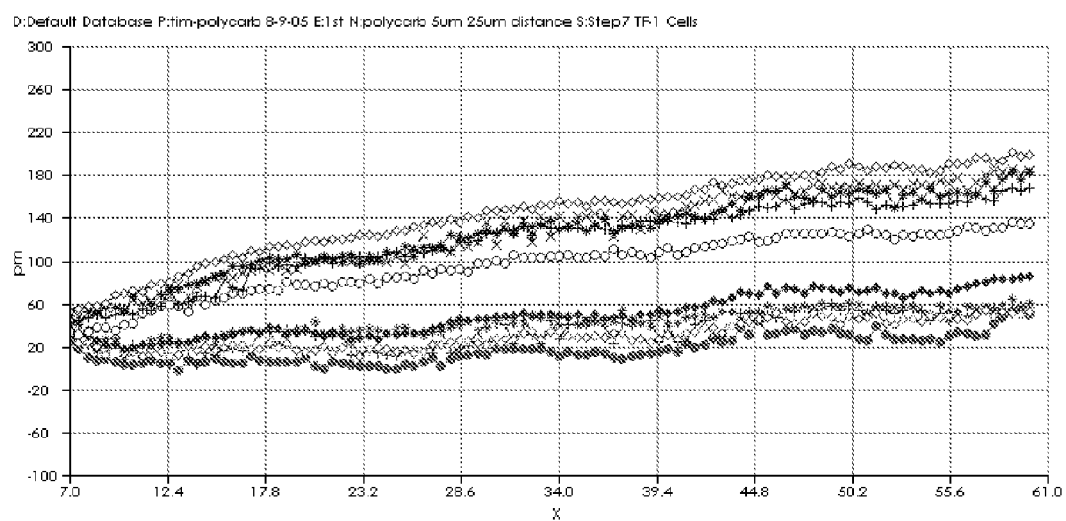
FIG. 7 shows a kinetic plot of an assay performed with sonicated and non-sonicated cells.
Figure 8:
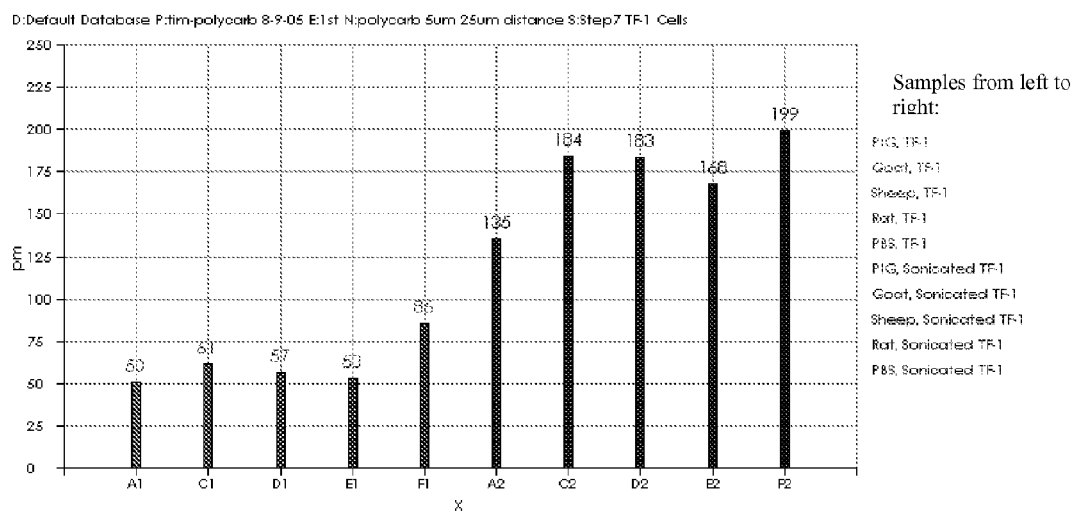
FIG. 8 shows an endpoint assay performed with sonicated and non-sonicated cells.

100,000 TF-1 cells were added to wells of the biosensor. Cells were untreated (the bottom four samples) or were sonicated 30 minutes (the top four samples) to lyse. A kinetic plot is shown in FIG. 7. An endpoint plot is shown in FIG. 8. The first column is pig, TF-1, the second column is goat, TF-1, the third column is sheep TF-1, the fourth column is rat TF-1, the fifth column is PBS, TF-1, the sixth column is pig, sonicated TF-1, the seventh column is goat, sonicated TF-1, the eighth column is sheep, sonicated TF-1, the ninth column is rat, sonicated TF-1, the tenth column is PBS, sonicated TF-1. The sonicated TF-1 cell wells have more debris that is passing through the membrane and binding to Protein A or IgG surfaces. TF-1 cells that are not sonicated have a non specific binding of 100 pm on Protein A. Sonicated cells have a non-specific binding of 50-86 pm on Protein A. Therefore, the integrated membrane has prevented the whole cells from coming down to the biosensor and interfering with the signal.

We claim:

1. A multiwell plate comprising:
   (a) a colorimetric resonant reflectance biosensor or a grating-based waveguide biosensor;
   (b) a first liquid impermeable sheet of a thickness of about 5 μm to about 1,000 μm, wherein the first liquid impermeable sheet has two or more holes; wherein the first liquid impermeable sheet is attached to a top surface of the colorimetric resonant reflectance biosensor or the grating-based waveguide biosensor;
   (c) a membrane attached to the top of the first liquid impermeable sheet, wherein the membrane covers all of the holes of the first liquid impermeable sheet;
   (d) a multiwell plate frame attached to the top of the membrane, wherein the multiwell plate frame has two or more holes and wherein the holes have a same size, number, and position as in the first liquid impermeable sheet such that a multiwell plate with an upper chamber and a lower chamber is formed by the colorimetric resonant reflectance biosensor or the grating-based waveguide biosensor, the first liquid impermeable sheet, the membrane, and the multiwell plate frame.

2. The multiwell plate of claim 1, wherein the colorimetric resonant reflectance biosensor or the grating-based waveguide biosensor, the first liquid impermeable sheet, the membrane, and the multiwell plate frame are all permanently attached to each other.

3. The multiwell plate of claim 1, wherein the colorimetric resonant reflectance biosensor or the grating-based waveguide biosensor and the first liquid impermeable sheet can be separated from the membrane and the multiwell plate frame.

4. The multiwell plate of claim 1, wherein the first liquid impermeable sheet is comprised of pressure sensitive adhesive, plastic or glass.

5. The multiwell plate of claim 1, wherein the membrane is comprised nylon, polyester, polycarbonate, or polysulphone.

6. The multiwell plate of claim 1, wherein in one or more specific binding substances or linkers are immobilized on the surface of the biosensor.

7. The multiwell plate of claim 1, wherein a second liquid impermeable sheet of a thickness of about 5 μm to about 1,000 μm is between the membrane and the multiwell plate frame, and wherein the second liquid impermeable sheet has two or more holes and wherein the holes have a same size, number, and position as in the first liquid impermeable sheet and the multiwell plate frame.

8. A method of detecting molecules that pass through an upper chamber of the multiwell plate of claim 1 to the lower chamber, comprising:
(a) detecting a first peak wavelength value (PWV) or a first effective refractive index for the lower chamber of a well of the multiwell plate;
(b) placing a test sample in the upper chamber of a well of the multiwell plate of claim 1;
(c) incubating the test sample;
(d) detecting a second PWV or a second effective refractive index for the lower chamber of a well of the multiwell plate; and
(e) comparing the first and second PWV or the first and second effective refractive index, wherein molecules that pass through an upper chamber of the multiwell plate are detected.

9. The method of claim 8, wherein the second PWV is detected in real-time.

10. The method of claim 9, wherein additional PWVs are detected.

11. The method of claim 8, wherein the molecules are a nucleic acid, peptide, protein solution, peptide solution, single or double stranded DNA, RNA, or RNA-DNA hybrid solution, a solution containing compounds from a combinatorial chemical library, a drug, antigen, polyclonal antibody, monoclonal antibody, single chain antibody (scFv), F(ab) fragment, F(ab')$_2$ fragment, Fv fragment, small organic molecule, large organic molecules, cell, virus, bacteria, polymer, nanoparticle, quantum dot, biological sample, or a combination thereof.

* * * * *